United States Patent [19]

Kaminsky et al.

[11] Patent Number: 5,024,984
[45] Date of Patent: Jun. 18, 1991

[54] CATALYSTS FOR THE OXIDATIVE CONVERSION OF METHANE TO HIGHER HYDROCARBONS

[75] Inventors: Mark P. Kaminsky, Lisle; Mark S. Kleefisch, Plainfield; George A. Huff, Naperville; Don M. Washecheck, Naperville; Aileen E. Alvarado-Swaisgood, Naperville; Mark K. Barr, Wheaton, all of Ill.

[73] Assignee: Amoco Corporation, Chicago, Ill.

[21] Appl. No.: 382,479

[22] Filed: Jul. 19, 1989

Related U.S. Application Data

[63] Continuation-in-part of Ser. No. 233,063, Aug. 17, 1988.

[51] Int. Cl.$^5$ .................................................. B01J 23/02
[52] U.S. Cl. .................................. 502/303; 502/300; 502/302; 502/341; 502/352
[58] Field of Search ............... 502/304, 341, 349, 340, 502/355, 352, 302, 300; 585/654, 500, 661, 700

[56] References Cited

U.S. PATENT DOCUMENTS

| | | | |
|---|---|---|---|
| 4,048,245 | 9/1977 | Pollitzer et al. | 260/668 |
| 4,444,984 | 4/1984 | Jones et al. | 585/500 |
| 4,560,821 | 12/1985 | Jones et al. | 585/500 |
| 4,608,449 | 8/1986 | Baerns et al. | 585/500 |
| 4,634,802 | 1/1987 | Jones et al. | 585/656 |
| 4,665,259 | 5/1987 | Brazdil et al. | 585/500 |
| 4,672,145 | 6/1987 | Kolts et al. | 585/658 |
| 4,780,449 | 10/1988 | Hicks | 502/303 |

Primary Examiner—William R. Dixon, Jr.
Assistant Examiner—James M. Hunter, Jr.
Attorney, Agent, or Firm—Nick C. Kottis; William H. Magidson; Ralph C. Medhurst

[57] ABSTRACT

An oxidative coupling catalyst composition for converting methane to a higher hydrocarbon comprising a mixed oxide of: a) a Group IIIB metal selected from the group consisting of yttrium, scandium and lanthanum; b) a Group IIA metal selected from the group consisting of barium, calcium and strontium; and c) a Group IVA metal selected from the group consisting of tin, lead and germanium and wherein the cationic species are present in the approximate ratio of 1:0.5–3:2–4, respectively, and an improved process employing same.

13 Claims, 4 Drawing Sheets

CATALYSTS FOR THE OXIDATIVE CONVERSION OF METHANE TO HIGHER HYDROCARBONS

CROSS-REFERENCE TO RELATED APPLICATION

This application is a continuation-in-part of commonly assigned, copending U.S. Ser. No. 233,063, filed Aug. 17, 1988 pending.

BACKGROUND OF THE INVENTION

This invention relates to oxidative coupling agents or catalysts for the conversion of methane to ethane, ethene and higher hydrocarbons having a greater molecular weight than methane.

In the search for petroleum, large amounts of natural gas are discovered in remote areas where there is no local market for it. The dominant technology now employed for utilizing remote natural gas involves its conversion to syngas, a mixture of hydrogen and carbon monoxide. While syngas processes fulfill the need for an easily transportable liquid that can be converted to several useful products, synthesis gas is an expensive intermediate. Oxygen is added to the rather inert methane molecule which is advantageous when products such as methanol or acetic acid are desired. In the case of hydrocarbons such as gasoline or diesel fuel, however, syngas processing requires the addition of oxygen, followed by its removal which increases final product cost.

Methane, the predominant component of natural gas, although difficult to activate can be reacted with oxygen or oxygen-containing compounds such as water or carbon dioxide to produce syngas. This mixture can be converted to syncrude such as with Fischer-Tropsch technology and then upgraded to transportation fuels using usual refining methods. Alternatively, syngas can be converted to liquid oxygenates which in turn can be converted to more conventional transportation fuels by catalysts such as certain zeolites.

Because syngas processing requires high capital investment, with the syngas being produced in energy wasteful ways as by steam reforming where fuel is burned to supply heat of reforming, and represents an indirect route to the production of hydrocarbons, other means of converting methane directly to higher hydrocarbons are needed.

Oxidative coupling has been recognized as a promising approach to the problem of methane conversion although the mechanism of action is not completely understood. In such processes, methane is contacted with solid materials referred to by various terms including catalysts, promoters, activators or contact materials. Methane mixed with oxygen and catalyst is directly converted to ethane, ethylene, higher hydroarbons and water. Carbon dioxide formation, which is highly favored thermodynamically, is undesirable as both oxygen and carbon are consumed without production of the desired higher value $C_{2+}$ hydrocarbons. In addition, in order to avoid complete combustion many methods for oxidative conversion have been carried out in the absence of an oxygencontaining gas, relying on the oxygen theoretically being supplied by the catalyst.

Catalytic mixtures of yttrium-barium-copper oxides are highly active and 100% selective for producing $CO_2$, that is, they are combustion catalysts. In order to obtain the required selectivity to hydrocarbon formation, Group IA metals, particularly lithium and sodium, have been used in such catalytic mixtures. Under the conditions used for oxidative coupling, however, migration and loss of the alkali metal normally occurs. Thus, the need for highly active, $C_{2+}$ hydrocarbon selective and stable oxidative coupling catalysts and improved processes employing same continues.

Many patents describe processes for converting methane to heavier hydrocarbons in the presence of reducible metal oxide catalysts. Most of these patents require or imply the need for a separate stage to re-oxidize the catalyst. These include U.S. Pat. No. 4,444,984 which teaches a reducible oxide of tin as a catalyst; U.S. Pat. No. 4,495,374 disclosing the use of any reducible oxide promoted by an alkaline earth metal; 4,523,049 showing a reducible oxide catalyst promoted by an alkali or alkaline earth, and requiring the presence of oxygen during the oxidative coupling reaction. U.S. Pat. No. 4,656,155 specifies yttrium in a mixture requiring zirconium and alkali metal. U.S. Pat. No. 4,450,310 claims coupling promoted by alkaline earth oxides in the total absence of molecular oxygen. U.S. Pat. No. 4,482,644 teaches a barium-containing oxygen-deficient catalyst with a perovskite structure. European Patent Application 198,251 covers a process conducted in the presence of free oxygen using a three component contact material of: (a) an oxide of calcium, strontium or barium, and optionally a material selected from the group consisting of chloride ions, compounds containing chloride ions, tin and compounds containing tin; (b) a sodium or potassium-containing material, and a Group IIA metal or a compound containing one, and optionally a material selected from the group consisting of chloride ions, compounds containing chloride ions, tin and compounds containing tin; (c) a Group IA metal compound, and optionally a material selected from the group consisting of chloride ions, compounds containing chloride ions, tin and compounds containing tin.

U.S. Pat. No. 3,885,020, although disclosing contact materials of the oxidative coupling type, is directed to a method of converting hydrocarbons to $CO_2$ and water for pollution control. The combustion catalysts used consist of four components: (1) zirconium, tin or thorium; (2) an alkaline earth material; (3) a rare earth-type element such as scandium, lanthanum or cesium; and (4) a metal of the first transition series.

Baerns U.S. Pat. No. 4,608,449 relates to a methane conversion process using a suitable metal oxide catalyst, including tin oxide, on an oxide catalyst carrier carried out under temperatures of from 500° C. to 900° C. in the presence of oxygen at specified pressure.

Hicks U.S. Pat. No. 4,780,449 discloses a catalyst for the conversion of methane to hydrogen, and higher hydrocarbons comprising a non-reducible metal oxide of Be, Mg, Ca, Sr, Ba, Sc, Y, La, Pr, Nd, Sm, Eu, Gd. Tb, Dy, Ho, Er, Tm, Yb and Lu which may be used alone or with up to 50% by weight of one or more promoter oxides of Li, Na, K, Be, Mg, Ca, Sr, Ba, Sc, Y, La, Ce, Pr, Nd, Sm, Eu, Gd, Tb, Dy, Ho, Er, Tm, Yb, Lu, Sn, Pb, Sb, Bi, Cu, Ag and Au. Methane conversion is carried out at temperatures of from 500° to 1000° C.

SUMMARY OF THE INVENTION

The present invention provides a three component catalyst for the oxidative conversion of methane to hydrocarbons containing 2 or more carbon atoms. The catalyst composition of this invention comprises a mixed oxide of: a) a Group IIIB metal selected from the group consisting of yttrium, lanthanum and scandium; b) a Group IIA metal selected from the group consisting of barium, calcium and strontium; and c) a Group IVA metal selected from the group consisting of tin, lead and germanium; and wherein the cationic species are present in the approximate ratio of 1:0.5-3:2-4, respectively. (All periodic table groupings are based on the CAS version of the periodic table).

A preferred catalyst composition comprises a mixed oxide of yttrium, barium and tin in which the cationic species, yttrium, barium and tin, are present in the approximate ratio of 1:2:3, respectively, and the catalyst composition is represented by the formula $Y_1Ba_2Sn_3O_y$ wherein y represents the number of oxygen anions required to balance the combined charge of cationic species Y, Ba and Sn when the cationic species barium is present solely as the oxide. When the cationic species is present as the carbonate, a preferred catalyst may be represented by the empirical formula $Y_1Ba_2Sn_3O_yC_z$ wherein z has a value of up to 2, and y represents the number of oxygen anions required to balance the combined charge of the cationic species, Y, Ba and Sn plus (3×z). A particularly preferred catalyst of this invention is represented by the formula wherein x is 0 when barium is present solely as an oxide and has a value of up to 4 when some of the barium species is present as the carbonate. For best results, it is preferred that x equal 0.

The catalysts of this invention are extremely stable at oxidative coupling conditions, thereby offering an advantage over the prior art technology.

In another embodiment, the invention provides an improved method for the oxidative coupling of methane to produce hydrocarbons containing 2 or more carbon atoms comprising contacting methane with a catalyst of this invention in the presence of oxygen. Process variable conditions including pressure, temperature, flow rate, feed gas composition and residence time are not believed critical and may be widely varied within suitable parameters. Conditions should be chosen to cause oxygen conversion to proceed near to, but short of completion in order to protect the catalyst from possible over reduction and degradation. This becomes particularly important at higher pressures and temperatures where increased catalytic activity will have to be compensated for by employing shorter contact times so as to avoid conditions of complete oxygen conversion, as illustrated in the examples. It is generally preferred to employ temperatures of from about 700°-900° C. and low operating pressures, preferably less than 250 psig, and most preferably atmospheric pressure.

At temperatures up to 800° C., residence times and relative feed rates are less critical. In operation, feed rates at room temperature and pressure (feed rate/catalyst rate) may be varied from 1000 cc/hr/gm-48,000 cc/hr/gm without affecting catalyst performance.

The feed preferably comprises pure methane or natural gas with sulfur species removed and oxygen premixed blends in ratios of 2:1 to 20:1 $CH_4$ to $O_2$. The feed may in addition include other species including nitrogen, carbon dioxide, carbon monoxide and water.

The contact solids may be maintained in the reaction zone as fixed, moving or fluidizing beds of solids. A fluidized bed operation is preferred because of its ability to handle highly exothermic reactions like methane oxidative coupling.

The catalyst of this invention may be prepared by any suitable method, such as dry-mixing followed by calcining. In the case of the $Y_1Ba_2Sn_3O_y$ catalyst, one presently preferred method comprises physically mixing yttrium carbonate, tin (II) acetate, and barium hydroxide, and specifically grinding the individual compounds together prior to calcining.

Another preferred method comprises preparing the $Y_1Ba_2Sn_3O_y$ catalyst of this invention in the substantial absence of carbon oxides, such as under a nitrogen or purified air, i.e., air from which $CO_2$ has been removed, other inert atmosphere. Additionally, since the presence of barium carbonates in the catalyst composition has been found to lead to lower C2+ selectivity in some cases, it may be advantageous to employ nitrates or hydroxides rather than carbonates as the source of barium or yttrium during preparation. Best results may be achieved when both carbonates and $CO_2$ are prevented from contacting the catalyst during the early stage of preparation. A benefit of this procedure is believed to be catalysts with less variation in performance, particularly when prepared in the absence of $CO_2$, which is normally present in air.

The source of tin is extremely important. It is preferred to employ tin (II) acetate which contains a relatively large amount of excess acetic acid, e.g., the tin (II) acetate contains between about 5-15% acetic acid. A preferred tin acetate can be purchased from Alpha Products. Use of tin acetate without the extra acetic acid produces a catalyst with much lower C2+ selectivity. For best results, it is preferred to employ tin (II) rather than tin (IV) source material.

BRIEF DESCRIPTION OF THE DRAWINGS

The invention will be more fully understood by reference to the following drawings, taken in conjunction with the description and claims, in which:

DETAILED DESCRIPTION OF PREFERRED EMBODIMENTS

The following examples further illustrate the invention.

EXAMPLE 1

Tin acetate, $Sn(C_2H_3O_2)_2$ (15.0 g, 0.06335 mole, from Alpha Products) was mixed with yttrium carbonate, $Y_2(CO_3)_3$—$3H_2O$ (4.12 g, 0.01 mole) and barium hydroxide, $Ba(OH)_2$—$8H_2O$ (12.74 g, 0.0404 mole) in a mortar and pestle. The solids were ground to a fine powder to homogenize the precursors. The hygroscopic nature of the solids resulted in the production of a white slurry upon grinding. After the slurry was thoroughly mixed, it was placed in a calcining furnace and heated to 700° C. at a rate of 4° C./min after which it was slowly heated to 800° C. at a rate of 2° C./min where it was held for five hours. The furnace was purged with a flow of air. The solid remained white after calcination. The preparation had a targeted composition of $YBa_2Sn_3O_y$.

EXAMPLE 2

Yttrium nitrate, $Y(NO_3)_3$—$6H_2O$ (11.5 g, 0.03 mole) was placed in a quartz crucible and heated to 150° C. in an oven until the solid melted. Barium hydroxide, Ba(OH)$_2$—$H_2O$ (11.7 g, 0.0618 mole) was added to the melt which was reheated to diffuse the hydroxide salt. After removal from the oven, the slurry solidified and lead nitrate, $Pb(NO_3)_2$ (29.8 g, 0.09 mole) was added and thoroughly mixed. The mixture was heated at a rate of 15° C./min to 600° C. and held there for 5 hours. The furnace was then cooled to 100° C. before the solids were removed. The sample was then calcined to 750° C. for 2 hours, cooled and calcined to 875° C. in air for 5 hours. The solid was black in color. The preparation had a targeted composition of $YBa_2Pb_3O_y$.

EXAMPLE 3

Barium hydroxide, $Ba(OH)_2$—$H_2O$ (35.1 g, 0.185 mole) was mixed together with lanthanum nitrate La(NO$_3$)$_3$—$6H_2O$ (39 g, 0.09 mole) and lead nitrate, $Pb(NO_3)_2$ (89.5 g, 0.27 mole). The components were ground to a fine powder before mixing together. The mixture was placed into a quartz crucible and 50 ml of distilled $H_2O$ added thereto, resulting in an orange slurry after the mixture was stirred and gently heated. Additional lanthanum nitrate and lead nitrate were added to the slurry to obtain the sought 1:2:3 stoichiometry. After some of the water was evaporated from the slurry by heating overnight at 120° C., the slurry was rehomogenized and heated to 180° C. overnight. The dry material was then placed in a furnace and heated at a rate of 15° C./min to 600° C. and maintained at that temperature for 1 hour. Thereafter, the temperature was raised at a rate 15° C./min to 700° C. The sample was held at 700° C. for 4 hours before cooling. A dark brown solid was obtained having the targeted composition of $LaBa_2Pb_3O_y$.

EXAMPLE 4

The catalyst of Example 1 was placed in a 9 mm internal diameter quartz tube reactor having a 3 mm outside diameter quartz thermowell. A premixed gas blend containing 40% by volume of methane, 4% by volume of oxygen and an inert carrier was employed. Nitrogen was used as an internal standard for conducting mass balances. 40–60 Mesh quartz (Vycor) was used to dilute the 14–40 mesh catalyst loading to obtain a more nearly isothermal bed. A relative feed rate of 1000 cc standard (at room temperature and pressure) of feed per hour per gram of catalyst was employed. Product gases were recycled to the front of the reactor and combined with fresh feed at a ratio of about 10:1 recycle to fresh feed. Methane conversion was determined by differences in outlet and inlet molar rates and also by moles of products formed. Oxygen was nearly completely consumed (98%+) for temperatures of from 600° to 750° C. $C_2+$ selectivity improved with increasing temperatures and reached about 50% at 750° C. The only other major carboncontaining product was $CO_2$.

EXAMPLE 5

The catalyst of Example 1 was retested following the method of Example 4 at a fixed temperature of 750° C.
and relative feed rates (feed rate/catalyst weight) of about 5, 10 and 15 times that used in Example 4. Even at these increased feed rates, oxygen consumption remained high (92-98%). $C_2+$ selectivity was relatively insensitive to these variations.

EXAMPLE 6

The catalyst of Example 3 was tested at the high relative flow rates employed in Example 5 (i.e. 15,000 cc/hour-gm). Selectivity was comparable to that of the catalyst of Example 1.

EXAMPLE 7

The catalyst of Example 2 was also tested at the high relative flow rates employed in Example 5. Performance was comparable, but not identical, to that of the catalyst of Example 3. This catalyst had a lower oxygen conversion rate at temperatures below 750° C. At 750° C. and at 600° C. after being at 700° C., the oxygen conversion rates were nearly identical, as were the selectivities.

EXAMPLE 8

The catalyst of Example 1 was tested at higher feed rates and temperatures, without recycling product gases. The feed composition was also varied. The reaction conditions are summarized below in Table I.

TABLE I

| Run | $CH_4:O_2$ | Space Velocity (cc/gm-hr) | Max Temp, °C. |
|---|---|---|---|
| 1 | 2:1 | 24,000 | 750 |
| 2 | 10:1 | 42,000 | 850 |
| 3 | 10:1 | 48,000 | 875 |

The first run showed little catalyst performance change over a 20 hour testing cycle. The feed was changed to a higher $CH_4:O_2$ ratio for runs 2 and 3. At 850° C. in run 2, selectivity to $C_2+$ reached about 68% with $CO_2$ making up most of the balance. Even at the high relative feed rates, near full oxygen conversion was observed. In run 3, both temperature and feed rate were increased. The catalyst began to change significantly at 875°. When the temperature was lowered to 850° C. after having been at 875° C., the catalyst showed a significant loss in $C_2+$ selectivity.

EXAMPLE 9

Bulk metals analysis of fresh and used $Y_1Ba_2Sn_3O_y$ catalyst prepared by the method of Example 1 was conducted using x-ray fluorescence (XRF). The results are listed below in Table II. As can be seen, for samples and 1 and 2, the Ba and Sn ratio and the elemental compositions for all three elements are within 10% of the fresh catalyst composition. For example 3, a correction must be applied due to the probable effect of the catalyst bed diluent used in the reactor test. Using the yttrium elemental analysis to estimate diluent amount, one must multiply the analyses by about 1.5 to get corrected valued. After doing so, the Sn value is within 10% of the fresh catalysts and the Ba value with within 15% of the fresh catalyst value. Thus, large, i.e. greater than 20%, losses of the elements are not observed with use.

TABLE II

| Sample | % Y | % Ba | % Sn | Stoichiometry |
|---|---|---|---|---|
| 1 (used) | 9.5 | 31 | 34 | $Y_1Ba_{2.1}Sn_{2.68}$ |

TABLE II-continued

| Sample | % Y | % Ba | % Sn | Stoichiometry |
|---|---|---|---|---|
| 2 (used) | 9.9 | 33 | 39 | $Y_1Ba_{2.16}Sn_{2.95}$ |
| 3 (used) | 6.4 | 18.2 | 22.5 | $Y_1Ba_{1.84}Sn_{2.63}$ |
| 4 (fresh) | 9.6 | 32 | 37 | $Y_1Ba_{2.16}Sn_{2.89}$ |

As expected, the tin is lower than targeted due to the presence of excess acetate in the tin acetate starting material. Not much difference was observed between some of the used catalyst and fresh catalyst indicating no large-scale metal leaching or volatilization.

EXAMPLE 10

$Y_1Ba_2Sn_3O_y$ catalyst (50 mg), prepared by the method of Example 1, was crushed to 80–100 mesh and diluted 15:1 with alumina and evaluated to determine oxygen conversion as a function of catalytic contact time (weight of catalyst per flow rate of gas feed) and temperature. Tests were conducted at 5 psig outlet and feed composition of 40% methane + 4% oxygen + 56% nitrogen. The tests were conducted in the order of lowest to highest temperature. Standard conditions (750° C., 5psig, 25 sccm=0.120 g catalyst-sec/cc feed at STP) were repeated after each temperature to assure that catalyst performance remained unchanged. The results are set forth in Table III below.

TABLE III

Repeat of Standard Conditions (750° C., 5 psig, 0.12 g cat-sec/cc, 56% $N_2$ + 40% $CH_4$ + 4% $O_2$)

| Condition | % Oxygen Conversion | % $C_2+$ Selectivity |
|---|---|---|
| Start-of-Run 750° C. | 88 | 55 |
| After Running at 775° C. | 88 | 54 |
| After Running at 800° C. | 86 | 53 |
| After Running at 825° C. | 89 | 54 |
| After Running at 875° C. | 87 | 52 |

At 750° C., $C_2+$ selectivity was relatively insensitive to oxygen conversion until reaching complete conversion, upon which $C_2+$ selectivity began to drop dramatically.

At 800° C., $C_2+$ selectivity declines as contact time increases, even at oxygen conversions of less than 100%. At the end of the run with 0.05 g of catalyst, $C_2+$ selectivity had declined about 65% at a contact time of 0.012 g catalyst-sec/cc gas.

At 850° C., $C_2+$ selectivity drops dramatically as contact time is increased.

EXAMPLE 11

Three samples of $Y_1Ba_2Sn_3O_y$ catalyst, A, B and C, respectively, were prepared by the method of Example 1 except the calcination temperatures of B and C were 1100° C. and 1550° C., respectively. Catalyst A was calcined at 800° C. as in Example 1. Testing of these three catalysts under the same conditions of 250 mg catalyst, 100 standard cc per minute of a preblended gas containing about 15% $CH_4$, 7.5% $O_2$, and balance $N_2$, at 750° C. gave the performance shown in Table IIIa.

TABLE IIIa

| Catalyst | Conversion % $O_2$ | Conversion % $CH_4$ | % $C_2+$ Selectivity |
|---|---|---|---|
| A | 95 | 27 | 22 |
| B | 100 | 29 | 20 |
| C | 20 | 5 | 0 |

For best performance in oxidative coupling, the catalysts should be calcined below 150° C. and preferably at less than 1100° C.

EXAMPLE 12

The effects of varying methane-to oxygen ratio on performance on the catalyst of Example 1 was investigated in a plug-flow reactor using 50 mg of catalyst at 5 psig, 100 sccm $CH_4$, 0 or 135 sccm $N_2$ which corresponds to 0% or 56% at nitrogen dilution, respectively, at both 750° C. and 800° C. The results are summarized in Tables IV and V below.

TABLE IV

Effect of Varying Methane-to-Oxygen Ratio on Performance with $Y_1Ba_2Sn_3O_y$ at 750° C.

| | | Methane-to-Oxygen Ratio | | |
|---|---|---|---|---|
| | | 5:1 | 10:1 | 18:1 |
| % Conversion | | | | |
| $O_2$ | 56% $N_2$ Dilution | 33 | 42 | 57 |
| | w/o $N_2$ | 49 | 62 | 77 |
| $CH_4$ | 56% $N_2$ Dilution | 5.2 | 4.5 | 4.2 |
| | w/o $N_2$ | 8.7 | 6.7 | 5.2 |
| % Selectivity | | | | |
| $C2+$ | 56% $N_2$ Dilution | 42 | 54 | 62 |
| | w/o $N_2$ | 38 | 52 | 64 |
| $C3+$ | 56% $N_2$ Dilution | 0.9 | 1.3 | 1.6 |
| | w/o $N_2$ | 1.2 | 1.9 | 2.3 |
| $C_2H_4$ to | 56% $N_2$ Dilution | 0.19 | 0.17 | 0.16 |
| $C_2H_6$ ratio | w/o $N_2$ | 0.41 | 0.34 | 0.29 |

TABLE V

Effect of Varying Methane-To-Oxygen Ratio on Performance with Y—Ba—Sn—O Catalyst at 800° C.

| | | Methane-to-Oxygen Ratio | | |
|---|---|---|---|---|
| | | 5:1 | 10:1 | 18:1 |
| % Conversion | | | | |
| $O_2$ | 56% $N_2$ Dilution | 59 | 74 | 89 |
| | w/o $N_2$ | 83 | 93 | 99 |
| $CH_4$ | 56% $N_2$ Dilution | 12.7 | 10.2 | 7.6 |
| | w/o $N_2$ | 16.4 | 11.7 | .8 |
| % Selectivity | | | | |
| $C2+$ | 56% $N_2$ Dilution | 57 | 68 | 74 |
| | w/o $N_2$ | 53 | 67 | 76 |
| $C3+$ | 56% $N_2$ Dilution | 3.0 | 3.4 | 3.1 |
| | w/o $N_2$ | 3.5 | 4.6 | 4.3 |
| $C_2H_4$ to | 56% $N_2$ Dilution | 0.49 | 0.40 | 0.31 |
| $C_2H_6$ ratio | w/o $N_2$ | 0.94 | 0.68 | 0.50 |

The data show that methane-to-oxygen ratios and temperature have significant impacts on conversion and selectivity. On the other hand, nitrogen dilution has little effect on $C_2+$ selectivity and appears to play a secondary role on conversion, presumably a kinetic rate effect, from altering reactant partial pressures. As the methane-to-oxygen ratio increases, methane conversion decreases whereas C2+ selectivity increases. The yield of C2+ hydrocarbons is simply the product of selectivity and conversion. The C3+ selectivity was slightly higher without nitrogen dilution.

EXAMPLE 13

$Y_1Ba_2Sn_3O_y$ catalyst prepared by the method of Example 1 was analyzed by XPS to determine metal ratios and oxidation states. Surface compositions, atomic ratios and electron binding energies (ebe) are reported in Tables VI–VII.

TABLE VI

| | Relative Atomic Percent of $Y_1Ba_2Sn_3O_y$ Catalyst | | | | |
|---|---|---|---|---|---|
| Run | O | $C_{total}$ | $C_{CO3}$ | Y | Ba | Sn |
| 1 | 50.8 | 10.7 | 1.6 | 14.7 | 8.8 | 14.9 |
| 2 | 47.5 | 25.1 | 3.8 | 8.0 | 6.4 | 13.0 |
| 3 | 55.6 | 6.1 | 1.2 | 10.8 | 9.9 | 17.6 |

TABLE VII

| | XPS Surface Stoichiometry | | | | | |
|---|---|---|---|---|---|---|
| | Target | | | Experimental | | |
| Run | Y | Ba | Sn | Y | Ba | Sn |
| 1 | 1 | 2 | 3 | 1 | 0.60 | 1.00 |
| 2 | 1 | 2 | 3 | 1 | 0.79 | 1.62 |
| 3 | 1 | 2 | 3 | 1 | 0.93 | 1.64 |

TABLE VIII

| | Electron Binding Energies (eV) of $Y_1Ba_2Sn_3O_y$ Catalyst | | | | | | | | |
|---|---|---|---|---|---|---|---|---|---|
| Run | O 1s | % | C 1s | % | Y 3d5/2 | % | Ba 3d5/2 | % | Sn 3d5/2 | % |
| 1 | 528.1 | 65 | 284.6 | 85 | 156.4 | 100 | 778.0 | 100 | 483.7 | 20 |
|   | 530.5 | 35 | 288.8 | 15 |       |     |       |     | 485.6 | 80 |
| 2 | 528.8 | 50 | 284.6 |    | 156.2 | 100 | 778.2 | 100 | 485.4 | 100 |
|   | 531.0 | 50 | 288.3 |    |       |     |       |     |       |    |
| 3 | 529.3 | 60 | 284.7 | 61 | 156.4 | 100 | 778.6 | 100 | 485.9 | 100 |
|   | 531.3 | 40 | 285.9 | 17 |       |     |       |     |       |    |
|   |       |    | 289.5 | 22 |       |     |       |     |       |    |

Repeat analyses on three portions of the sample gave variable compositions (Table VI) indicating heterogeneity of the catalyst. Yttrium surface enrichment, as indicated by the Sn/Y and Ba/Y ratios of Table VII, causes the Y:Ba:Sn ratios to differ from the target bulk value 1:2:3. The ratios obtained from the three samples vary slightly; yet, they reflect barium and tin depletion. Note, for instance, that the first run in Table VI has a stoichiometry consistent with the tin pyrochlore ($Y_2Sn_2O_7$) which has been identified by x-ray diffraction (XRD). Tin is present in two or three chemical states, Sn 3d 5/2 ebe's of 483.7 eV and 485.6 eV indicates elemental tin (20%) and $Sn^{+2}$ and/or $Sn^{+4}$ (80%), respectively (Table VIII). This result is in excellent agreement with XRD data. Only one portion of the three analyzed contained elemental tin. This could be indicative of tin oxidation or sample heterogeneity. The Sn 3d ebe's are usually low when compared to literature and experimental XPS data of the pure compounds, indicating that tin formed a compound with yttrium and barium. The Ba 3d 5/2 of 778.2 eV is too low to indicate the presence of $BaCO_3$ and BaO (ebe's 779.0 and 779.7 eV, respectively) as reported in Table VIII. Y 3d ebe's of all samples were at 156.5 ± 0.3 eV. Literature reports the same values for $Y_2O_3$. Two oxygen species with ebe's at approximately 528.1 and 530.0 eV were found (Table VIII). The former species is typical for metal oxides. The latter is too low for adsorbed oxygen and could be representative for the specific compound formed by barium, tin and yttrium.

EXAMPLE 14

A portion of a sample of the catalyst of Example 1 was mounted on an scanning electron microscope (SEM) stub. In addition, another portion of sample was embedded in epoxy and the cross-section exposed by grinding and polishing and also by cutting the embedded sample with a diamond knife on the ultramicrotome. The sample was then examined in the SEM uncoated, and subsequently coated with gold in the vacuum evacuator. At X10,000 magnification, the areas examined of the uncoated sample show grainy particles ranging in size from 500 Å to 3000 Å in diameter. Some of the crystals appeared to be oriented perpendicular to the plane of the other crystals.

SEM-EDX elemental analysis dot maps were obtained of the cross-section areas. Y and Ba appear uniformly distributed, but the Sn rich areas appear to be concentrated in small clumps throughout the sample.

EXAMPLE 15

A longer term stability test was conducted % in a recycle reactor wherein the reactor gases were well backmixed with 50 mg of the $Y_1Ba_2Sn_3O_y$ catalyst of Example 1 at 750° C., 3 psig and 120,000 cc/gm hr SV of 40% $CH_4$ + 4% $O_2$ + 56% $N_2$. The run lasted nearly 10 days without any change in selectivity or conversion, other than that accountable by changing feed gas cylinders. Studies of the used catalyst are described below.

Studies have shown that there are several characteristics of the $Y_1Ba_2Sn_3O_y$ metal oxide catalyst of this invention that classify it as a unique composition. STEM/EDX characterization showed a distinct change in the homogeneity of the composition throughout the used catalyst compared to fresh catalysts. Depending on the reaction conditions, varying degree of homogeneity could be obtained with the most homogeneous samples being produced under total oxygen conversion or above 875° C. When coupled with XRD analysis, the STEM/EDX data present a model of the catalyst being a crystalline barium stannate ($BaSnO_3$) which is coated or in solid solution with an amorphous oxide/carbonate mixture of yttrium and barium, represented by $YBaC_zO_y$. The resulting mixture is unique.

To illustrate this increase in homogeneity of the used catalyst, the composition at several points in the catalyst, as determined by STEM/EDX, was plotted on a ternary phase diagram. In FIGS. 1–4, $YO1.5$, BaO, and $SnO_2$ are at the three corners and the composition at any point in the diagram can be determined where the point intersects the tie lines for each of the elements. The tie lines are in the units of mole%. For example, a composition represented by the point in the phase diagram that intersects the 30% line of BaO, the 20% line of YO1.5 and the 50% line of SnO2 has 30 mole % BaO, 20 mole % YO1.5 and 50% SnO2, or $Y_1Ba_{1.5}Sn_{2.5}O$.

Figure 1:
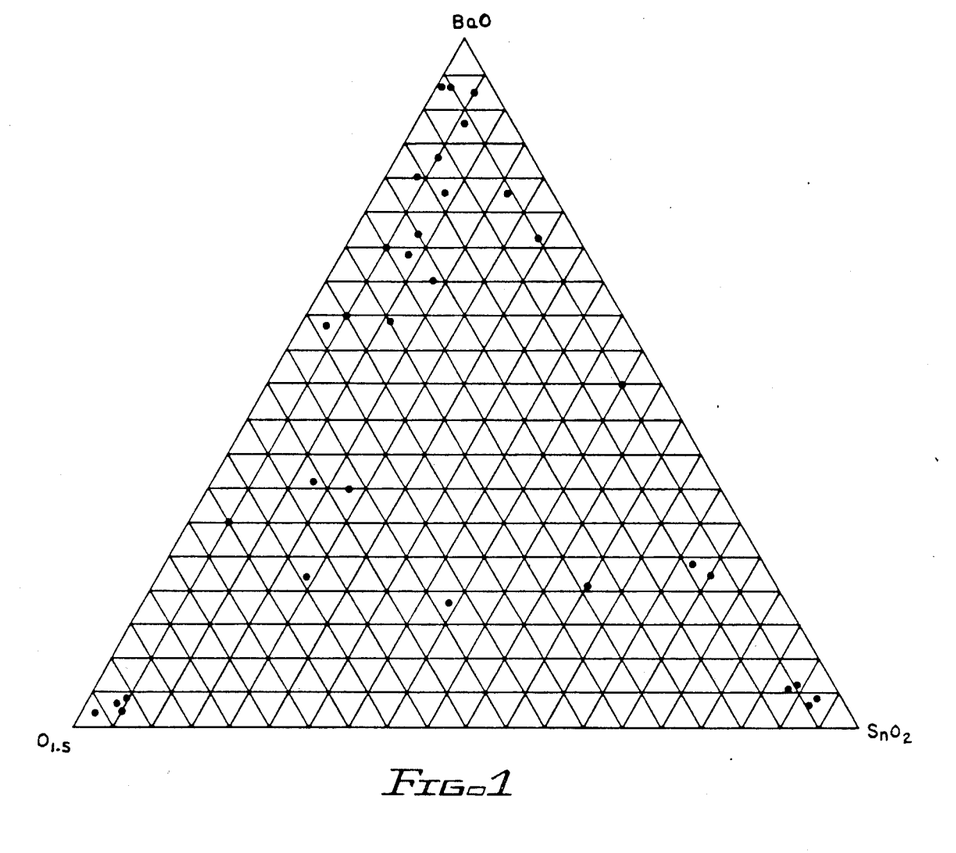
FIG. 1 is a STEM/EDX ternary phase diagram of fresh $Y_1Ba_2Sn_3O_y$ catalyst.

Referring to the drawings, FIG. 1 is STEM/EDX ternary phase diagram of the distribution of compositions observed in the fresh $Y_1Ba_2Sn_3O_y$ catalyst. A large degree of scatter indicates the heterogeneity of the catalyst. Virtually pure BaO, $Y_2O_3$ and $SnO_2$ were observed along with mixtures of the three metal oxides.

Figure 2:
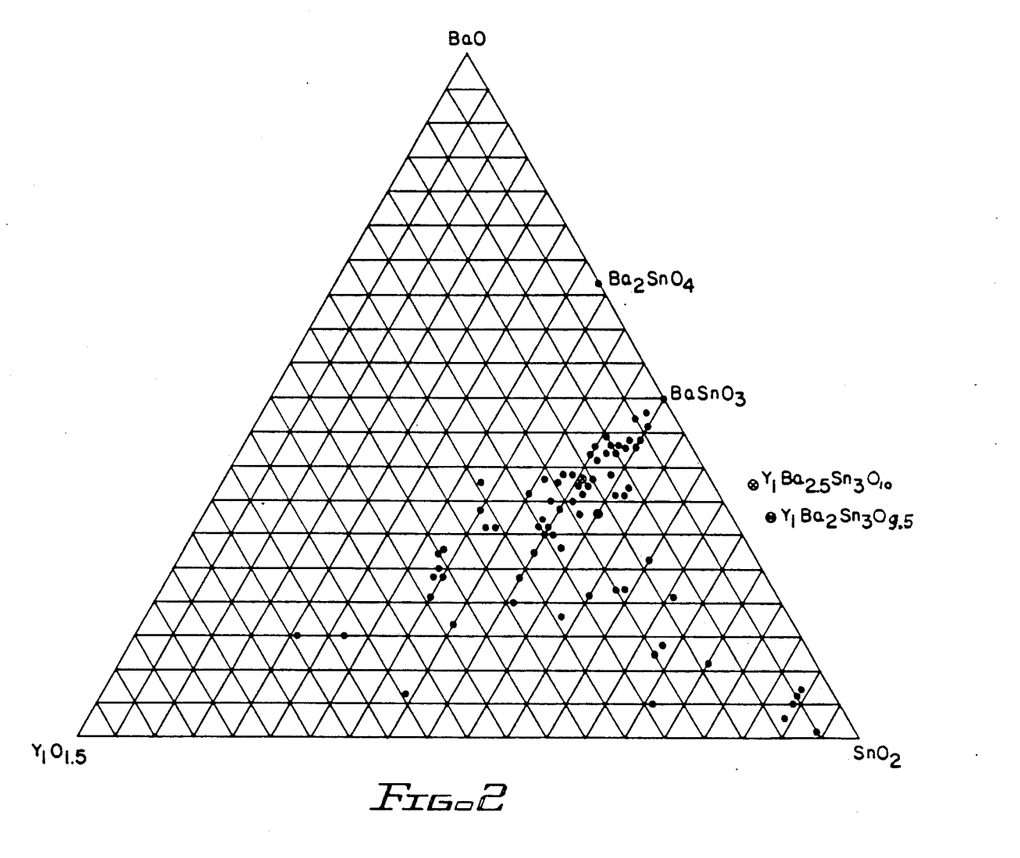
FIG. 2 is a STEM/EDX ternary phase diagram of used $Y_1Ba_2Sn_3O_y$ catalyst that has not been exposed to reducing conditions.

FIG. 2 is a STEM/EDX ternary phase diagram of a used catalyst that has not been exposed to reducing conditions.

A majority of the compositions fall on the tie line between $BaSnO_3$ and $YO_{1.5}$ and the region below it. Many areas converge around the $Y_1Ba_2Sn_3O_y$ nominal composition even though there is no crystalline phase with this composition. $BaSnO_3$ is the major phase in this material with minor amounts of $SnO_2$ which are also observed by STEM/EDX. The only way areas can have a composition of $Y_1Ba_2SnO_3$ is to have an amorphous coating or solid solution of yttria, barium carbonates and tin oxides on crystalline $BaSnO_3$.

Figure 3:
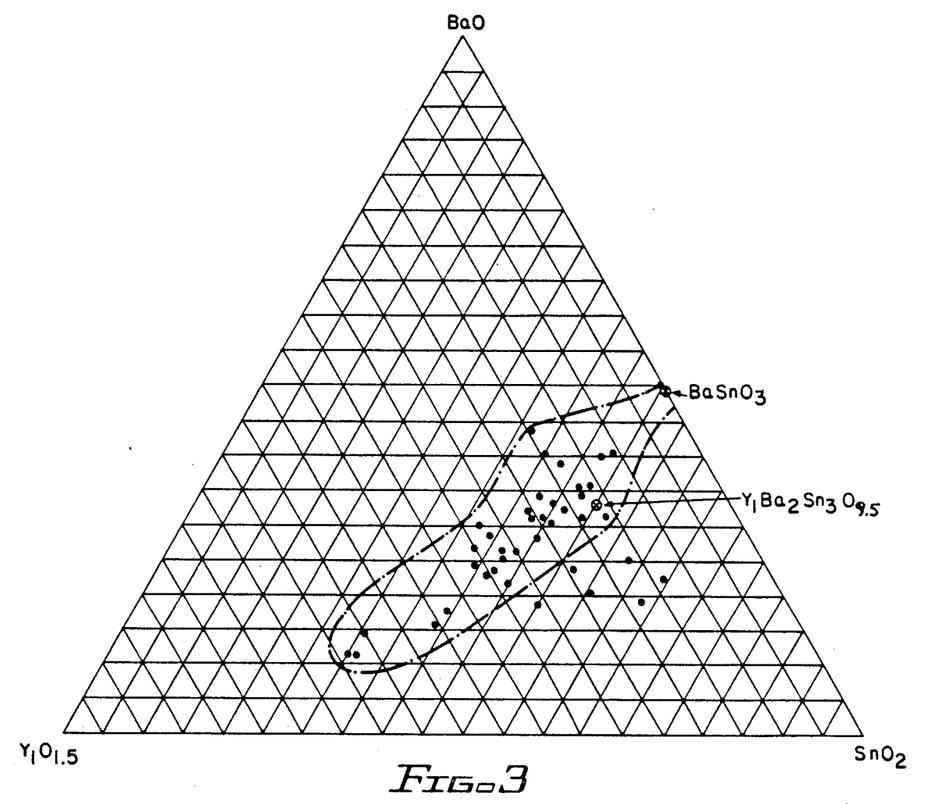
FIG. 3 is a STEM/EDX ternary phase diagram of used $Y_1Ba_2Sn_3O_y$ catalyst that has been exposed to reducing conditions.

FIG. 3 is a ternary phase diagram of a catalyst that has been exposed to reducing conditions (100% $O_2$ conversion) at 750° C. The homogeneity of the composition has increased in this sample such that most areas fall just below the $BaSnO_3$, $YO_{1.5}$ tie line and in closer proximity to the crystalline phase so the majority of the areas contain a crystalline $BaSnO_3$ which is coated or in solid solution with an amorphous oxide/carbonate mixture of yttrium and barium.

Figure 4:
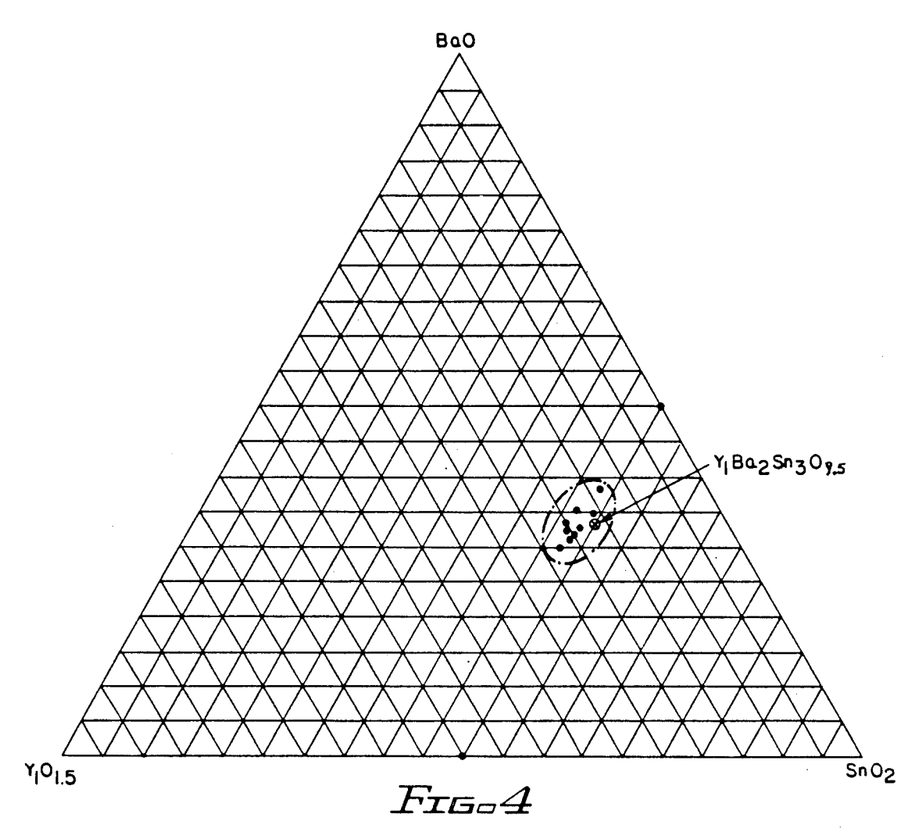
FIG. 4 is a STEM/EDX ternary phase diagram of used $Y_1Ba_2Sn_3O_y$ catalyst that has been exposed to severe reducing conditions.

FIG. 4 is a STEM/EDX ternary phase diagram of a catalyst that has been exposed to severe reducing conditions. Extreme reducing conditions at 875° C. further homogenized the catalyst composition as seen in FIG. 4. The distribution centers exclusively on the $Y_1Ba_2Sn_3O_y$ composition even though by XRD, the major crystalline phase is $BaSnO_3$.

The region of the phase diagram that the composition of the used catalyst falls in is:

$(BaO)_a(YO_{1.5})_b(SnO_2)_c$ wherein 5% < a < 50%; 0% < b < 57%; and 25% < c < 90%.

Depending upon the catalyst preparation, XPS analysis of the catalyst indicates apparent enrichment of the surface with either barium in the form of carbonate or oxide or yttria. Smaller amounts of tin were detected on the surface in part due to the Sn aggregating into small $SnO_2$ particles. Unusually high hydrogen consumption was observed in the TPR/TPO analysis of $Y_1Ba_2Sn_3O_y$ catalyst along with trends in reduction temperature verses catalyst activity. All of these unique characteristics are described more fully in the following examples.

EXAMPLE 16

Analytical electron microscopy shows distinct differences in fresh and used $Y_1Ba_2Sn_3O_y$ catalysts which evidence the unique nature of the material. A histogram of selected areas were analyzed in both the fresh and used catalysts by Energy Dispersive X-Ray (EDX) in the STEM mode. After calibrating with known standards, the metal composition could be quantitated in these different areas. A fresh catalyst was very heterogeneous in composition with regions of pure $BaCO_3$, $SnO_2$ and $Y_2O_3$ observed along with mixtures of the various elements. Depending on the reaction conditions, the catalyst becomes more homogeneous in Y, Ba and Sn composition. Severe reaction conditions such as total oxygen conversion and greater than 875° C. reaction temperatures cause the most dramatic changes and also caused the catalyst to lose selectivity to $C_2+$. Virtually all particles analyzed had close to the nominal composition $Y_1Ba_2Sn_3O_y$. This is unusual in that the XRD showed only $BaSnO_3$ as the major phase. Therefore, it is believed that the catalyst may be characterized as an amorphous/crystalline mixture where the only significant crystalline phase is $BaSnO_3$ and the amorphous phase is a $YBaO_x$ oxide which homogeneously coats or forms a solid solution with the $BaSnO_3$. The combination of $BaSnO_3$ and $YBaO_x$ phases forms a uniquely uniform material.

Less severe conditions also caused the catalyst to become more homogeneous in composition yet still retain its selectivity to $C_2+$ hydrocarbons. For example, at 97% oxygen conversion, 800° C., 5:1 $CH_4/O_2$ feed at 120,000 cc/gmhr SV and 4 hours reaction time, a large fraction of the areas had a composition near $Y_1Ba_2Sn_3O_y$. A majority of areas followed the tie line from $BaSnO_3$ to $Y_2O_3$, indicating varying amounts of $Y_2O_3$ are in solid solution or coating the $BaSnO_3$.

Elemental x-ray mapping of the used catalyst also confirmed the compositional homogeneity of the catalyst.

High resolution TEM showed lattice fringes on the $Y_1Ba_2Sn_3O_y$ catalyst which had been used at full oxygen conversion. At magnifications greater than 1,000,000X, fringe spacings of 5.5Å, 7Å and 12.2Å were observed. These are larger that pure $BaSnO_3$ at 4.117Å and $Y_2Sn_2O_7$ at 10.4Å. The expanded lattice seen in the TEM suggest some small particles which have incorporated other materials into the lattice such as yttria, i.e. solid solutions. $BaCO_3$ has cell dimensions of a=5.134Å, b=8.9Å and c=6.43Å, some of which are similar to those observed by TEM.

All used catalysts show an increase in the homogeneity of composition, suggesting a unique mixture of crystalline and amorphous phase.

EXAMPLE 17

X-Ray Diffraction Analysis

A sample of $Y_1Ba_2Sn_3O_y$ catalyst was calcined to 800° C. for 5 hours in air which resulted in a complex mixture of barium carbonate ($BaCO_3$), tin oxide ($SnO_2$) and minor poorly crystalline phases of barium stannate ($BaSnO_3$) and yttrium tin pyrochlore ($Y_2Sn_2O_7$). As shown in Example 18, Sn119 NMR chemical shifts suggested that neither the $Y_2Sn_2O_7$ nor the $BaSnO_3$ were solid solutions. Further calcination to 1100° C. increased the crystallinity and concentration of $BaSnO_3$ yet changed the catalysts selectivity to more combustion products. A significant decrease in $BaCO_3$ was also observed at this temperature. Further calcination to 1400° C. caused the disappearance of $BaCO_3$ and the major phases are now $BaSnO_3$ and a $Ba(Y)SnO_3$ solid solution which has an expanded cell of 4.1354Å. Pure $Y_2Sn_2O_7$ was also present. The material stayed with this composition until the calcining temperature was close to 1700° C. at which the sample melted and reacted with the alumina crucible. $SnO_2$ observed in fresh catalysts had a preferred orientation such that the 101 and 202 XRD diffraction intensities were much greater than the intensities published in the powder diffraction files. Bulk $SnO_2$ prepared by calcination of the Sn(II) acetate starting materials also has the preferred orientation shown by the 101 and 202 reflection intensity enhancement. This feature is common to the oxidative coupling catalysts but is also found in $SnO_2$, a combustion catalyst prepared from tin acetate.

Depending on the reaction conditions, the used catalysts had significantly higher crystallinity and were more pure in $BaSnO_3$ than the fresh catalysts. The catalyst was in effect being crystallized to $BaSnO_3$ by being used for methane oxidative coupling. The higher the oxygen conversion, the larger the effect on the catalyst. For that matter, catalysts that had been heated too hot or run under reducing conditions (100% oxygen conversion) were some of the most crystalline with the major phase being pure $BaSnO_3$ along with minor phases of $Y_2Sn_2O_7$ solid solution, $SnO_2$, and another poorly crystalline $BaSnO_3$ solid solution phase. Barium carbonate, which was a major phase in the fresh catalyst had decomposed to form $BaSnO_3$ in the catalyst used at full oxygen conversion. $BaCO_3$ only exists in traces in the used catalyst. The amount of carbonate in the used catalysts depends on the severity of operation. The solid solution of $Y_2Sn_2O_7$ had an expanded cubic cell constant of 10.430(4)Å compared to the known value of 10.373Å. The minor phase of $BaSnO_3$ solid solution had a cubic cell constant of 4.1209Å compared to the known cell constant of 4.1163Å. Expansion of the unit cell in both $Y_2Sn_2O_7$ and $BaSnO_3$ is caused by yttria substituting for the smaller tin ion in the structure, thus creating a solid solution with yttria.

EXAMPLE 18

Sn119 Solid State NMR

NMR analysis of fresh $Y_1Ba_2Sn_3O_y$ catalyst showed, that at the sensitivity of NMR, only known tin compounds were in the fresh catalyst. When calcined to 920° C., $SnO_2$ and a fairly broad peak for $BaSnO_3$ were observed. In a good, non-over reduced catalyst, the Sn 119 NMR is only slightly different from the fresh catalyst. A small increase in the $BaSnO_3$ peak was observed in the used catalyst. An 1100° C. calcination sharpened the $BaSnO_3$ peak, indicating better crystallinity, and a $Y_2Sn_2O_7$ pyrochlore was the only other species present. Integrated areas under these peaks corresponded well with XRD results in estimating compositions.

EXAMPLE 19

Thermal Gravimetric Analysis

The fresh $Y_1Ba_2Sn_3O_y$ catalyst of Example 1 was calcined to about 800°-1000° C. in air. The material showed a gradual weight loss of about one (1) weight percent when heated to 800°-900° C. Such a small weight loss is attributed to the catalyst desorbing moisture or other volatile compounds adsorbed from the atmosphere and possible evolution of $CO_2$ from $BaCO_3$ decomposition at about 800° C. Cooling back to room temperature in dry air did not cause the catalyst to regain any of its lost weight.

EXAMPLE 20

The catalyst of Example 1 was tested at 750° C. in a recycle reactor wherein the gases were well backmixed to illustrate the effect of complete oxygen conversion on selectivity to C2+ hydrocarbons. The feed was 10:1 $CH_4/O_2$ + 56% nitrogen and the pressure was held at 3 psig. Two experiments were conducted so as to obtain a wide variation in contact time (grams of catalyst/sec/cc gas at STP): one with 0.5 gram catalyst and the other with 0.05 gram catalyst. Each run was made in the order of lowest to highest contact time. Selectivity to C2+ hydrocarbons remains relatively constant until reaching a contact time of about 0.5; thereafter, C2+ selectivity decreases as contact time increases. Upon reaching the longest contact time of 6, the initial contact time of 0.3 was repeated for the run with 0.5 gram catalyst. The C2+ selectivity returned to 45% which is 10% below the original value of 55%, implying catalyst deactivation. Part of the fall off in C2+ selectivity at contact times about 0.5 is attributed to the intrinsic response of the catalyst at high oxygen conversion; however, part of the drop is an accumulative, non-reversible decline from catalyst aging caused by reduction and degradation at complete oxygen conversion.

EXAMPLE 21

A carbonate free $Y_1Ba_2Sn_3$ oxide catalyst was prepared by grinding $Y(NO_3)_3.6H_2O$ (2.30 g), $Ba(OH)_2.8H_2O$ (3.79 g) and $Sn(OCOCH_3)_3$ (4.2 g) under air or nitrogen to form a soft paste. The paste was extruded and fired in air at 100° C., 200° C., 300° C., 400° C., 500° C., 600° C. and 700° C. for 15–30 minutes at each temperature, then heated at 800° C. for 5 hours under air flow. The catalyst was then calcined at 900° C. for 2 hours, the temperature was reduced to 800° C. and the catalyst was calcined at that temperature for 2 hours. X-ray diffraction of the fresh catalyst showed $BaSnO_3$ as major, $Y_2O_3$ and $BaCO_3$ (Witherite phase) as intermediate, and $SnO_2$ as a minor crystalline material.

EXAMPLE 22

The catalyst of Example 21 was ground and sieved to pass through a 180 mesh sieve and be held on a 250 mesh sieve. 50 milligrams of the catalyst, diluted with about 500 mg of alpha alumina, was tested with a fresh feed blend of 30% $CH_4$, 6% $O_2$, 56% $N_2$ at 100 standard cc per minute rate at 800° C. Ultra high purity gases were used. In addition, 250 cc/minute of the product gas at room temperature was recycled to the front of the unit. Near complete oxygen conversion was obtained (97%) and 20% of the methane was converted. Carbon atom selectivities were 59% to hydrocarbons with 2 or more carbon atoms, 2% to carbon monoxide, and 39% to carbon dioxide.

Although embodiments of this invention have been shown and described, it is to be understood that various modifications and substitutions, as well as rearrangement and combination of parts, components, equipment and/or process steps can be made by those skilled in the art without departing from the novel spirit and scope of this invention.

What is claimed is:

1. An oxidative coupling catalyst composition for converting methane to a higher hydrocarbon comprising a mixed oxide of: a) a Group IIIB metal selected from the group consisting of yttrium, lanthanum and scandium; b) a Group IIA metal selected from the group consisting of barium, calcium and strontium; and c) a Group IVA metal selected from the group consisting of tin, lead and germanium and wherein the cationic species of the Group IIIB metals, the Group IIA metals and the Group IVA metals are present in the approximate ratio of 1:0.5–3:2-4, respectively.

2. A catalyst composition of claim 1 wherein the cationic species are present in an approximate ratio of 1:2:3, respectively.

3. A catalyst composition of claim 1 wherein said mixed oxide is a mixed oxide of yttrium, barium and tin.

4. A catalyst composition of claim 3 wherein the cationic species are present in an approximate ratio of 1:2:3, respectively.

5. A catalyst composition of claim 1 represented by the formula $Y_1Ba_2Sn_3O_y$ wherein y represents the number of oxygen anions required to balance the combined charge of the cationic species Y, Ba and Sn.

6. A catalyst composition of claim 1 represented by the formulae $$(Y_2O_3)(BaO)_{4-x}(BaCO_3)_x(SnO_2)_6$$

wherein x is 0 when the cationic species barium is present as the oxide and has a value up to 4 when barium carbonate is present.

7. The catalyst of claim 1 wherein said catalyst exhibits an amorphous coated crystalline phase.

8. A process for preparing a catalyst represented by the approximate empirical formula $Y_1Ba_2Sn_3O_y$ wherein the value of y represents the number of oxygen anions required to balance the combined charge of the cationic species Y, Ba and Sn, comprising intimately mixing an oxygen-containing compound of each of yttrium, barium and tin, and thereafter calcining said mixture at a temperature of up to about 1000° C. to produce said catalyst.

9. The process of claim 8 wherein yttrium carbonate, barium hydroxide and tin (II) acetate with a stoichiometric excess of acetic acid are employed to produce said catalyst.

10. The process of claim 8 wherein said catalyst is prepared in the substantial absence of carbon oxides.

11. The process of claim 9 wherein said catalyst is prepared in the substantial absence of carbon oxides.

12. The process of claim 9 wherein yttrium nitrate is used in place of yttrium carbonate.

13. The process of claim 11 wherein yttrium nitrate is used in place of yttrium carbonate.

* * * * *